(12) United States Patent
McLaren et al.

(10) Patent No.: US 6,433,005 B1
(45) Date of Patent: Aug. 13, 2002

(54) BENZOFURAN AND BENZOTHIOPHENE DERIVATIVES AS ANTI-INFLAMMATORY AGENTS

(75) Inventors: Kevin L. McLaren, Carmel, IN (US); David Bernard Smith, San Mateo; Jahari Laurant Tracy, Redwood City, both of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/006,349

(22) Filed: Dec. 3, 2001

Related U.S. Application Data

(60) Provisional application No. 60/251,283, filed on Dec. 5, 2000.

(51) Int. Cl.[7] ................ A61K 31/381; C07D 307/85; C07D 333/70
(52) U.S. Cl. ............... 514/443; 514/470; 549/55; 549/466
(58) Field of Search ............... 514/443, 470; 549/55, 466

(56) References Cited

U.S. PATENT DOCUMENTS

| | | |
|---|---|---|
| 3,331,854 A | 7/1967 | Huffman et al. |
| 4,621,091 A | 11/1986 | Tischler et al. |
| 4,663,347 A | 5/1987 | Atkinson et al. |
| 4,745,127 A | 5/1988 | Atkinson et al. |
| 4,822,803 A | 4/1989 | Atkinson et al. |
| 4,933,351 A | 6/1990 | Atkinson et al. |
| 5,426,113 A | 6/1995 | Low |
| 5,731,342 A | 3/1998 | Cullinan et al. |

FOREIGN PATENT DOCUMENTS

| | | |
|---|---|---|
| DE | 33 42 624 A1 | 3/1984 |
| WO | WO 95/02406 | 1/1995 |

Primary Examiner—Joseph K. McKane
Assistant Examiner—Sonya Wright
(74) Attorney, Agent, or Firm—Gloria Pfister

(57) ABSTRACT

This invention relates to compounds, which are generally anti-inflammatory and analgesic compounds, and which are represented by Formula I:

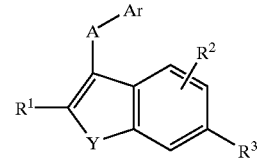

wherein A is a —$CH_2$—, —C(O)—, —O—, —S—, —S(O)—, or —$S(O)_2$— and the other substituents are as defined in the specification; or prodrugs, individual isomers, mixtures of isomers, and pharmaceutically acceptable salts thereof. The invention further relates to pharmaceutical compositions containing such compounds and methods for their use as therapeutic agents.

16 Claims, No Drawings

BENZOFURAN AND BENZOTHIOPHENE DERIVATIVES AS ANTI-INFLAMMATORY AGENTS

CROSS-REFERENCE TO RELATED APPLICATION

This Application claims benefit under Title 35 U.S.C. 119(e) of U.S. Provisional Application No. 60/251,283 filed Dec. 05, 2000.

BACKGROUND OF THE INVENTION

1. Field of the Invention

This invention relates to anti-inflammatory and analgesic compounds, especially to certain benzofuran and benzothiophene derivatives, pharmaceutical compositions containing them, methods for their use, and methods for preparing these compounds.

2. Background of the Invention

Non-steroidal anti-inflammatory drugs (NSAIDs), have a problem of causing serious side-effects such as gastrointestinal tract distress or nephro-toxicity. NSAIDs inhibit the activity of cyclooxygenase (COX), which is an enzyme involved in prostaglandin G/H synthesis, resulting in the inhibition of the biosynthesis of prostaglandins not only in inflammatory loci but also in stomach and kidney. It has been found that COX exists in two forms: COX-1 and COX-2, *Cell*, 83, 345, (1995).

COX-1 is expressed in normal cells and controls the function of stomach and kidney, while COX-2 is induced by mitogens or cytokines in inflammatory sites where inflammation and other immunoreactions occur, *J. Biol. Chem.*, 271, 33157(1996).

To avoid the toxicity of NSAIDs due to the inhibition of coexisting COX-1, selective inhibitors of COX-2 have been investigated. The selective COX-2 inhibitors have anti-inflammatory action, pain-relieving action, and/or anti-pyretic action; with less side effects such as bleeding in the gastrointestinal tract. COX-2 inhibitors may show anticancer activity and lower the induction of asthma in asthmatic patients who are sensitive to conventional NSAIDs. These selective inhibitors of COX-2 may also be used in treating Alzheimer's disease and osteoporosis of women after menopause.

3. Description of Related Art

U.S. Pat. No. 3,331,854 (American Cyanamid) refers to certain novel furan and thiophene compounds.

U.S. Pat. No. 5,426,113 (Warner Lambert) refers to certain tetrazol-benzothiophene carboxamides in preventing ulcer formation.

U.S. Pat. No. 5,731,342 (Eli Lilly) refers to certain benzothiophenes, which are useful for the treatment of the medical indications associated with post-menopausal syndrome and breast cancer treatment and prevention.

U.S. Pat. Nos. 4,663,347; 4,745,127; 4,822,803; 4,933,351; and 4,621,091 (Merck) refer to certain benzofuran-2-carboxylic acid derivatives as 5-lipoxygenase inhibitors.

U.S. Pat. No. 4,621,091 (Merck) refers to certain 3-hydroxybenzothiophene-2-sulfide derivatives as 5-lipoxygenase inhibitors.

DE Pat. No. 3,342,624 (Grote) refers to certain 3-hydroxybenzoyl-benzofuran derivatives.

PCT Published Application No. WO 95/02406 (Warner Lambert) refers to certain use of benzothiophene and benzofuran compounds for monitoring inflammation.

SUMMARY OF THE INVENTION

In a first aspect, this invention provides compounds selected from the group of compounds represented by Formula I:

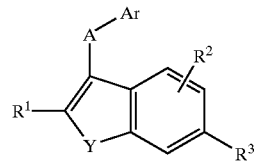

wherein:

Y is O or S;

A is a —$CH_2$—, —C(O)—, —O—, —S—, —S(O)—, or —$S(O)_2$—;

Ar is an optionally substituted phenyl;

$R^1$ is hydrogen, alkyl, alkoxy, hydroxy, halo, cyano, —C(O)$NR^4R^5$, —$COOR^4$, —$NR^4R^5$, wherein $R^4$ and $R^5$ are each independently in each occurrence hydrogen or alkyl;

$R^2$ is hydrogen, alkyl, alkoxy, hydroxy, halo, haloalkyl, nitro, cyano, or —$NR^4R^5$, wherein $R^4$ and $R^5$ are as defined previously;

$R^3$ is —$SR^6$, —$SOR^6$, —$SO_2R^6$, or —$SO_2NR^4R^5$ wherein $R^6$ is alkyl, hydroxyalkyl, alkoxyalkyl, carboxyalkyl, or alkoxycarbonylalkyl; and $R^4$ and $R^5$ are as defined previously; or prodrugs, individual isomers, mixtures of isomers, and pharmaceutically acceptable salts thereof.

In a second aspect, this invention provides pharmaceutical compositions containing a therapeutically effective amount of a compound of Formula I or its pharmaceutically acceptable salt and a pharmaceutically acceptable excipient.

In a third aspect, this invention provides a method of treatment of a disease, in particular an inflammatory and autoimmune disease, in a mammal treatable by administration of a prostaglandin G/H synthase inhibitor, comprising administration of a therapeutically effective amount of a compound of Formula I or its pharmaceutically acceptable salt.

In a fourth aspect, this invention provides processes for preparing compounds of Formula I.

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, n-propyl, 2-propyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, benzyloxy, pyridin-2-ylmethyloxy, and the like.

"Alkoxycarbonylalkyl" means a radical —$R^aC(O)R^b$ where $R^a$ is an alkylene group as defined above and $R^b$ is an alkoxy group as defined above e.g., methoxycarbonylethyl, ethoxycarbonylbutyl, and the like.

"Aryl" means a monovalent monocyclic or bicyclic aromatic radical of 6 to 10 ring atoms which is substituted independently with one to five substituents, preferably one, two, or three substituents selected from alkyl, cycloalkyl, cycloalkylalkyl, halo, nitro, cyano, hydroxy, alkoxy, amino, acylamino, alkylamino, dialkylamino, haloalkyl, haloalkoxy, heteroalkyl, —COR (where R is hydrogen, alkyl, cycloalkyl, cycloalkylalkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the derivatives thereof.

"Halogen" or "halo" means the radical fluoro, bromo, chloro, and/or iodo.

"Haloalkyl" means alkyl substituted with one or more same or different halo atoms, e.g., —CH$_2$Cl, —CF$_3$, —CH$_2$CF$_3$, —CH$_2$CCl$_3$, and the like, and further includes those alkyl groups such as perfluoroalkyl in which all hydrogen atoms are replaced by fluorine atoms.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-hydroxymethyl-2-methylpropyl, 2-hydroxybutyl, 3-hydroxybutyl, 4-hydroxybutyl, 2,3-dihydroxypropyl, 1-hydroxymethyl-2-hydroxyethyl, 2,3-dihydroxybutyl, 3,4-dihydroxybutyl and 2-hydroxymethyl-3-hydroxypropyl, preferably 2-hydroxyethyl, 2,3-dihydroxypropyl and 1-hydroxymethyl-2-hydroxyethyl. Accordingly, as used herein, the term "hydroxyalkyl" is used to define a subset of heteroalkyl groups.

"Optionally substituted phenyl" means a phenyl ring which is optionally substituted independently with one to four substituents, preferably one or two substituents selected from alkyl, cycloalkyl, cycloalkylalkyl, halo, nitro, cyano, hydroxy, alkoxy, amino, acylamino, monoalkylamino, dialkylamino, haloalkyl, haloalkoxy, heteroalkyl, —COR (where R is hydrogen, alkyl, phenyl or phenylalkyl, —(CR'R")$_n$—COOR (where n is an integer from 0 to 5, R" and R' are independently hydrogen or alkyl, and R is hydrogen, alkyl, cycloalkyl, cycloalkylalkyl, phenyl or phenylalkyl), or —(CR'R")$_n$–CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" has the meaning conventionally associated with it in synthetic organic chemistry i.e., an atom or group capable of being displaced by a nucleophile and includes halo (such as chloro, bromo, iodo), alkanesulfonyloxy, arenesulfonyloxy, alkylcarbonyloxy (e.g. acetoxy), arylcarbonyloxy, mesyloxy, tosyloxy, trifluoromethanesulfonyloxy, aryloxy (e.g., 2,4-dinitrophenoxy), methoxy, N,O-dimethylhydroxyamino, and the like.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, t-butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Prodrugs" means any compound which releases an active parent drug, or any compound which changes its oxidation level, according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may also be prepared by incomplete oxidation of certain functional groups, such as sulfur containing functional groups, in such a way that the oxidation of said functional group may be effected in vivo to release a compound according to Formula I. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives) or carbamates (e.g., N,N-dimethylaminocarbonyl) of hydroxy functional groups and thiol or sulfoxide groups in compounds of Formula I, and the like.

"Protecting group" refers to a grouping of atoms that when attached to a reactive group in a molecule masks, reduces or prevents that reactivity. Examples of protecting groups can be found in T. W. Greene and P. G. Wuts, *Protective Groups in Organic Chemistry*, (Wiley, 2nd ed. 1991) and Harrison and Harrison et al., *Compendium of Synthetic Organic Methods*, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitroveratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers, and allyl ethers.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or di-substituted with the s alkyl group and situations where the heterocyclo group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn, Ingold and Prelog, (Cahn et al. *Angew. Chem.* Inter. Edit., 5, 385; (1966) errata 511; Cahn et al. *Angew. Chem.*, 78, 413;(1966) Cahn and Ingold *J. Chem. Soc.* (London), 612; (1951) Cahn et al. *Experientia*, 12, 81;(1956), Cahn, *J. Chem.Educ.*, 41, 116, (1964)) or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of "Advanced Organic Chemistry", 4th edition J. March, John Wiley and Sons, New York, 1992).

Throughout the application the following abbreviations are used with the following meanings:

| | |
|---|---|
| DBN | 1,5-Diazabicyclo[4.3.0]non-5-ene |
| DBU | 1,8-Diazabicyclo[5.4.0]undec-7-ene |
| DMF | N,N-Dimethylformamide |
| DMSO | Dimethylsulfoxide |
| EtOAc | Ethyl acetate |
| $Et_2O$ | Ethyl ether |
| EtOH | Ethanol |
| HMPA | Hexamethylphosphoric triamide |
| HPLC | High pressure liquid chromatography |
| KHMDS | Potassium hexamethyldisilazide |
| MCPBA | m-Chloroperbenzoic acid |
| MHz | Megahertz |
| MS | Mass Spectrum |
| NMR | Nuclear Magnetic Resonance |
| OXONE ™ | Potassium peroxymonosulfate |
| p-TsOH | p-Toluenesulfonic acid |
| TFAA | Trifluoroacetic anhydride |
| THF | Tetrahydrofuran |
| TLC | Thin layer chromatography |

Nomenclature

The naming and numbering of the compounds of this invention is illustrated below.

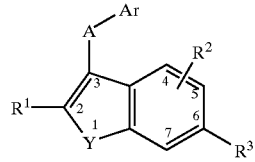

Formula I

In general, the nomenclature used in this Application is based on AUTONOM™ v.4.0, a Beilstein Institute computerized system for the generation of IUPAC systematic nomenclature.

Representative Compounds of this Invention are as Follows:
Compound of Formula I wherein $R^1$, $R^2$, $R^3$, Y, A, and Ar are as defined below:

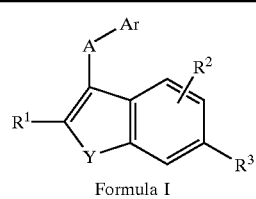

Formula I

| Cpd # | $R^1$ | $R^2$ | $R^3$ | A | Y | Ar | MS $[m + H]^+$ |
|---|---|---|---|---|---|---|---|
| 15 | CN | H | methylsulfonyl | —O— | —S— | 4-methoxyphenyl | 360 |
| 16 | CN | H | methylsulfonyl | —S— | —S— | 4-methoxyphenyl | 376 |

-continued

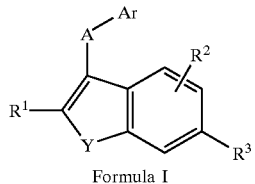

Formula I

| Cpd # | R¹ | R² | R³ | A | Y | Ar | MS [m + H]⁺ |
|---|---|---|---|---|---|---|---|
| 17 | CN | H | methylsulfonyl | —S— | —S— | 2-chlorophenyl | 381 |
| 18 | CN | H | methylsulfonyl | —S— | —S— | 4-methylphenyl | 360 |
| 19 | CN | H | methylsulfonyl | —S— | —S— | 2,4-dichlorophenyl | 415 |
| 20 | CN | H | methylsulfonyl | —O— | —S— | 4-fluorophenyl | 348 |
| 21 | CN | H | methylsulfonyl | —S— | —S— | phenyl | 346 |
| 22 | CN | H | methylsulfonyl | —S— | —S— | 4-methylphenyl | 344 |
| 23 | CN | H | methylsulfonyl | —S— | —S— | 4-chlorophenyl | 381 |
| 24 | CN | H | methylsulfonyl | —O— | —S— | phenyl | 330 |
| 25 | CN | H | methylsulfonyl | —O— | —S— | 2-chloro-4-methoxyphenyl | 394 |
| 26 | CN | H | methylsulfonyl | —S— | —S— | 4-fluorophenyl | 364 |
| 27 | CN | H | methylsulfonyl | —S— | —S— | 2-fluorophenyl | 348 |
| 28 | CN | H | methylsulfonyl | —S— | —S— | 2,6-dichlorophenyl | 415 |
| 29 | CN | H | methylsulfonyl | —O— | —S— | 2-methoxyphenyl | 360 |
| 30 | CN | H | methylsulfonyl | —S— | —S— | 2-fluorophenyl | 364 |
| 31 | CN | H | methylsulfonyl | —O— | —S— | 4-ethoxyphenyl | 374 |
| 32 | CN | H | methylsulfonyl | —S— | —S— | 2,4-difluorophenyl | 382 |
| 33 | CN | H | methylsulfonyl | —O— | —S— | 4-chloro-2-fluorophenyl | 383 |
| 34 | CN | H | methylsulfonyl | —O— | —S— | 2,4-difluorophenyl | 366 |
| 35 | CN | H | methylsulfonyl | —S— | —O— | 4-methoxyphenyl | 360 |
| 36 | CN | H | methylsulfonyl | —S— | —O— | 2,4-difluorophenyl | M+ = 366 |

Preferred Embodiments

While the broadest definition of this invention is set forth in the Summary of the Invention, certain compounds of Formula I are preferred.

In certain preferred embodiments Ar is a phenyl optionally substituted at one or more postions, preferably with one to two substitutents independently selected from the group consisting of halo and alkoxy, and $R^3$ is —$SO_2R^6$, wherein $R^6$ is alkyl.

In another embodiment, another preferred group of compounds is that wherein Ar is phenyl optionally substituted at one or more positions, preferably with one to two sybstitutents independently selected from the group consisting of halo and alkoxy; $R^3$ is —$SO_2R^6$, wherein $R^6$ is alkyl; Y is —O—; and A is —S—; and yet a more preferred group of compounds is that wherein Ar is phenyl optionally substituted at one or more positions, preferably with one to two substitutents independently selected from the group consisting of halo and alkoxy; $R^3$ is —$SO_2R^6$, wherein $R^6$ is alkyl; Y is O; A is S; and $R^1$ is alkyl or cyano.

In another embodiment another preferred group of compounds is that wherein Ar is phenyl optionally substituted at one or more positions, preferably with one to two substitutents independently selected from the group consisting of halo and alkoxy; $R^3$ is —$SO_2R^6$; wherein $R^6$ is alkyl; Y is —S—; and A is —S—; and yet a more preferred group of compounds is that wherein Ar is phenyl optionally substituted at one or more positions preferably with one to two substitutents independently selected from the group consisting of halo and alkoxy; $R^3$ is —$SO_2R^6$, wherein $R^6$ is alkyl; Y is S; A is S; and $R^1$ is alkyl or cyano.

Within the foregoing preferred embodiment another preferred group of compounds is that wherein Ar is phenyl optionally substituted at one or more positions, preferably with one to two substitutents independently selected from the group consisting of halo and alkoxy; $R^3$ is —$SO_2R^6$, wherein $R^6$ is alkyl; Y is —S—; and A is —O—; and yet a more preferred group of compounds is that wherein Ar is phenyl optionally substituted at one or more positions, preferably with one to two substitutents independently selected from the group consisting of halo and alkoxy; $R^3$ is —$SO_2R^6$, wherein $R^6$ is alkyl; Y is S; A is O; and $R^1$ is alkyl or cyano.

While the broadest definition of the invention is set forth in the Summary of the Invention, certain compounds of Formula I are preferred. For example, preferred compounds of Formula I are those in which $R^1$ is cyano or alkyl, $R^2$ is hydrogen or alkyl, $R^3$ is alkylsulfonyl, A is —S— or —O—, Y is —S— or —O—, and Ar is unsubstituted, monosubstituted, or disubstituted phenyl. Even more preferred compounds of Formula I are those in which A is —S—or —O—, Y is —S—, $R^1$ is cyano, $R^2$ is hydrogen, $R^3$ is alkylsulfonyl, and Ar is a phenyl mono or disubstituted with halo or alkoxy.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as *Fieser and Fieser's Reagents for Organic Synthesis*, Volumes 1–17 (John Wiley and Sons, 1991); *Rodd's Chemistry of Carbon Compounds*, Volumes 1–5 and Supplementals (Elsevier Science Publishers, 1989); *Organic Reactions*, Volumes 1–40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

A person of ordinary skill in the art will have no difficulty, having regard to that skill and this disclosure, in determining how to synthesize compounds of this invention.

Preparation of Compounds of Formula I

Schemes A, and B, describe methods to prepare the compounds of Formula I.

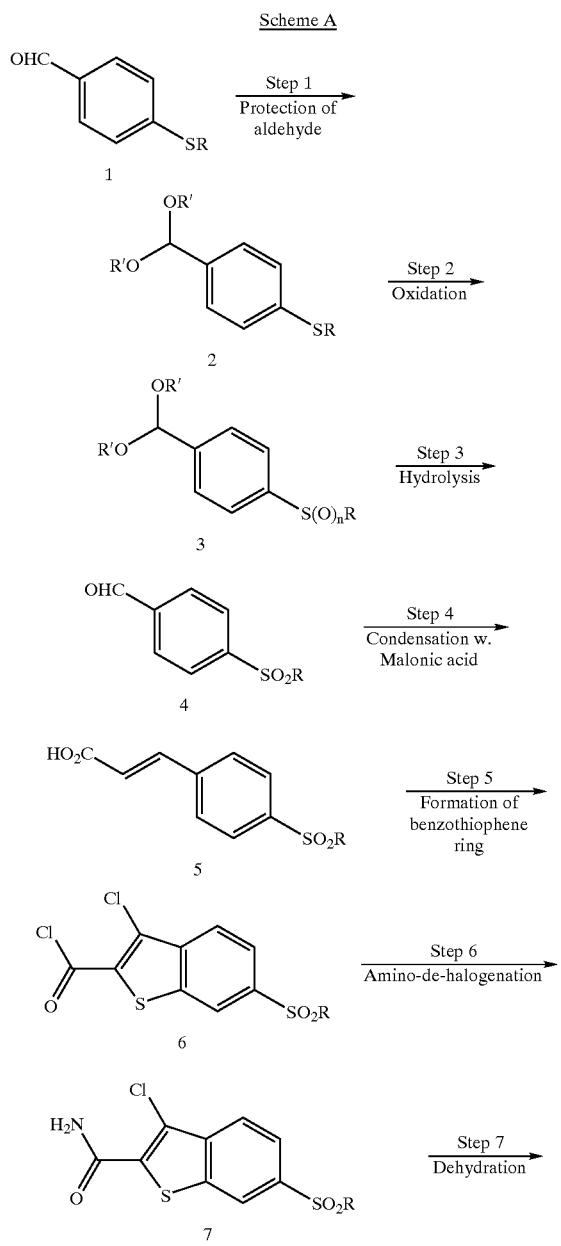

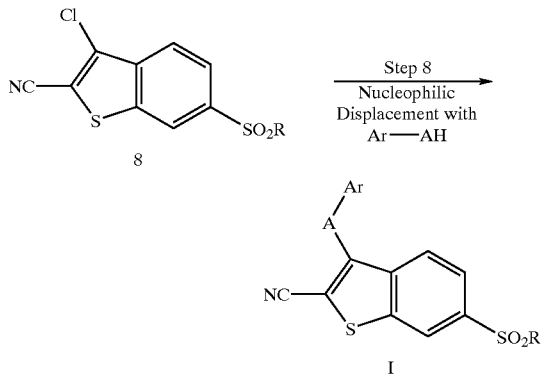

Scheme A describes the synthesis of a compound of Formula I wherein A is —S— or —O—; Y is —S—; R and R' are alkyl; $R^1$ is cyano; n is one or two, $R^2$, $R^3$ and Ar are as defined in the Summary of the Invention.

In Step 1, a certain aldehyde of Formula 1, wherein R is alkyl, preferably wherein R is methyl, can be protected by treatment with an alcohol such as methyl alcohol, in the presence of an acid catalyst such as p-TsOH, to give an acetal of Formula 2, preferably 1-(1,1-dimethoxy-methyl)-4-methylsulfanyl-benzene. In general, the compounds of Formula 1 are commercially available or can be readily synthesized by those of ordinary skill in the art ,see e.g., Watabe, et al, *J.Chem.Soc.Chem.Commun.*; 10; 1983; 585–586.

In Step 2, the —SR group of a certain compound of Formula 2 wherein R and R' are alkyl, preferably wherein R and R' are methyl, can be oxidized with MCPBA, OXONE™, and the like to provide a sulfoxide or sulfone of Formula 3, wherein R and R' are alkyl, preferably R and R' are methyl. Suitable solvents for the reaction are alcohols (such as methanol and ethanol) or halogenated solvents (such as dichloromethane, chloroform and the like). Sulfoxides of Formula 3 may be similarly converted to the corresponding sulfones. It is appreciated that this second oxidation may be performed at various points in Scheme A as may be required by the skilled artisan.

In Step 3, a certain acetal of Formula 3, wherein R and R' are alkyl, preferably wherein R and R' are methyl, can be hydrolyzed with a suitable amount of acid, such as diluted hydrochloric acid or sulfuric acid in a suitable inert solvent such as THF, to give an aldehyde of Formula 4, wherein R is alkyl, preferably wherein R is methyl.

In Step 4, a certain aldehyde of Formula 4, wherein R is alkyl, preferably wherein R is methyl, can be condensed with malonic acid in the presence of pyridine or an alkoxide as a catalyst, preferably pyridine to give a 3-(4-alkylsulfonyl-phenyl)-acrylic acid of Formula 5, wherein R is alkyl, preferably wherein R is methyl, according to the method of Wiley, R. H.; Smith, N. R. *Org. Synth. Coll.* Vol IV, 731–734. Suitable solvents are inert solvents such as THF and the like.

In Step 5, a certain intermediate acid chloride of Formula 6, wherein R is alkyl, preferably wherein R is methyl, can be prepared according to the method of Connor, D. T., et al. *J. Med. Chem.* 1992, 35, 958–65; wherein the acrylic acid of Formula 5, wherein R is alkyl, preferably wherein R is methyl, can then be converted to the benzothiophene of Formula 6, wherein R is alkyl, preferably wherein R is methyl, by treatment with $SOCl_2$ in the presence of pyridine in suitable solvents such as polar aprotic solvents, e.g. DMF, DMSO, chlorobenzene and the like.

In Step 6, a certain acid chloride of Formula 6, wherein R is alkyl, preferably wherein R is methyl, can be amino-dehalogenated with ammonia in THF or an halogenated solvent such as dichloromethane, chloroform, and the like, to give a certain amide of Formula 7, wherein R is alkyl, preferably wherein R is methyl.

In Step 7, a certain amide of Formula 7, wherein R is alkyl, preferably wherein R is methyl, can be dehydrated preferably in the presence of an anhydride such as trifluoroacetic anhydride, trifluoromethanesulfonic anhydride, and the like in an halogenated solvent, such as dichloromethane, chloroform, and the like to give the nitrile of Formula 8, wherein R is alkyl, preferably wherein R is methyl.

In Step 8, a nucleophilic displacement of the chlorine atom of a certain compound of Formula 8, wherein R is alkyl, preferably wherein R is methyl, by a certain phenol or thiophenol of Formula Ar—AH wherein A is —O— or —S—, in the presence of a base such as potassium hydroxide, potassium hexamethyldisilazide and the like, in an inert solvent such as DMF can give the 3-substituted-2-cyano-6-alkylsulfoxy-benzothiophene of Formula I, wherein R is alkyl, preferably wherein R is methyl.

Scheme B

Scheme B describes the synthesis of a compound of Formula I wherein A is —S— or —O—, Y is —O—, $R^1$ is cyano, $R^2$, $R^3$ and Ar are as defined in the Summary of the Invention. Within this scheme the groups R, R' and R" are each independently of each other preferably alkyl groups.

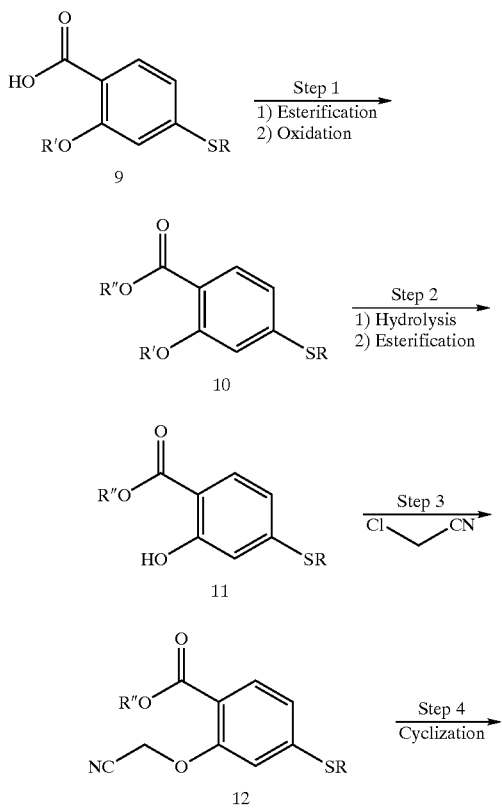

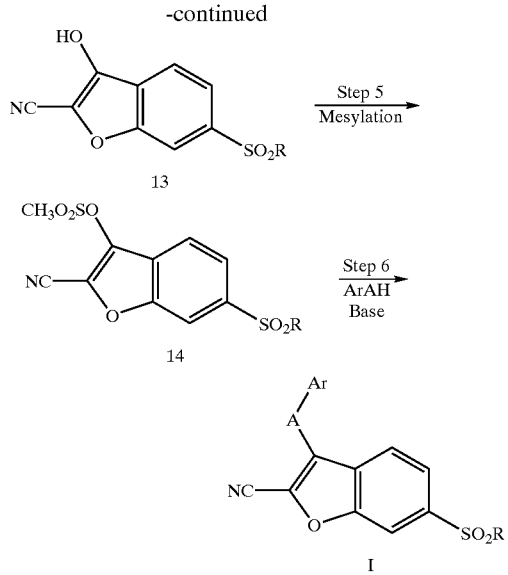

In Step 1, a certain acid of Formula 9 can be esterified by conditions well known in the art, i.e. with an alcohol under acidic conditions. Subsequently the —SR group can be oxidized with MCPBA, OXONE™, and the like to provide a sulfoxide or sulfone of Formula 10. Sulfoxides of Formula 10 may be similarly converted to the corresponding sulfones. It is appreciated that this second oxidation may be performed at various points in Scheme B as may be required by the skilled artisan.

Suitable solvents are alcohols such as methanol or ethanol or halogenated solvents such as dichloromethane, chloroform, and the like.

In Step 2, the ether and ester groups of a certain compound of Formula 10 can be hydrolyzed with acid reagents such as pyridinium hydrochoride, boron trichloride, hydrobromic acid, and the like, preferably pyridinium hydrochloride, and the acid group can be further esterified by conditions well known in the art to give a compound of Formula 11.

In Step 3, the phenol group of a certain compound of Formula 11 can be alkylated with chloroacetonitrile under basic conditions, in a suitable inert solvent such as DMF, DMSO, benzene, toluene, and the like. A suitable base can be sodium carbonate, potassium carbonate, triethylamine, and the like.

In Step 4, a certain compound of Formula 13 can be obtained by internal cyclization to form a benzofuran ring. Such cyclization can be effected with potassium tert-butoxide in an inert solvent such as toluene.

In Step 5, the hydroxyl group of a certain compound of Formula 13 can be protected by mesylation with methane sulfonyl chloride under basic conditions to provide a certain compound of Formula 14.

In Step 6, a nucleophilic displacement of the mesylate group of a certain compound of Formula 14 by a certain optionally substituted benzenethiol of Formula Ar—AH in the presence of sodium hydride in an inert solvent or a mixture of solvents such as THF or DMF, can give a compound of Formula I, wherein A is S or O, and Y is O.

General Utility

The compounds of the invention are inhibitors of prostaglandin G/H Synthase I and II (COX I and COX II), especially COX II, in vitro, and as such are expected to possess both anti-inflammatory and analgesic properties in vivo. See, for example, Goodman and Gilmans's "*The Pharmacological Basis of Therapeutics*", Ninth Edition, McGraw Hill, New York, 1996, Chapter 27. The compounds and compositions containing them are therefore useful as anti-inflammatory and analgesic agents in mammals, especially humans. They find utility in the treatment of fever, inflammation, and pain caused by conditions such as rheumatic fever, symptoms associated with influenza or other viral infections, low back and neck pain, dysmenorrhoea, headache, dental pain, sprains, strains, sports injuries, bursitis, tendonitis, myositis, synovitis, arthritis (rheumatoid arthritis and osteoarthritis), gout, ankylosing spondylitis, burns, or injuries. They may be used to inhibit prostanoid-induced smooth muscle contractions (e.g., in the treatment of dysmenorrhoea, premature labor, and asthma) and to treat autoimmune disorders (such as systemic lupus erythematosus and type I diabetes).

As inhibitors of prostaglandin G/H Synthase, the compounds of this invention are also expected to be useful in the prevention and treatment of cancer, in particular colon cancer. It has been shown that COX-2 gene expression is upregulated in human colorectal cancers and that drugs that inhibit prostaglandin G/H Synthase are effective in animal models of cancer (Eberhart, C. E., et. al., *Gastroenterology*, 107, 1183–1188, (1994), and Ara, G. and Teicher, B. A., *Prostaglandins, Leukotrienes and Essential Fatty Acids*, 54, 3–16, (1996)). In addition, there is epidemiological evidence that shows a correlation between use of drugs that inhibit prostaglandin G/H synthase and a reduced risk of developing colorectal cancer (Heath, C. W. Jr., et. al., *Cancer*, 74, No. 10, 2885–8, (1994)).

The compounds of this invention are also expected to be useful in the prevention and treatment of Alzheimer's disease. Indomethacin, an inhibitor of prostaglandin G/H synthase, has been shown to inhibit the cognitive decline of Alzheimer's patients (Rogers, J., et. al., *Neurology*, 43, 1609, (1993)). Also, the use of drugs which inhibit prostaglandin G/H synthase has been linked epidemiologically with a delayed onset of Alzheimer's disease (Breitner, J. C. S., et. al., *Neurobiology of Aging*, 16, No. 4, 523, (1995) and *Neurology*, 44, 2073, (1994)).

Testing

The anti-inflammatory activity of the compounds of this invention may be assayed by measuring the ability of the compound to inhibit COX I and COX II, especially COX II, in vitro, using a radiometric assay, as described in more detail in Example 4. It may also be assayed by in vivo assays such as the Rat Carrageenan Paw and Rat Air-Pouch assays, as described in more detail in Examples 5 and 6. The analgesic activity of the compounds of this invention may be assayed by in vivo assays such as the Randall-Selitto assay and the rat arthritis pain model, as described in Example 7.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula I may range from approximately 0.005–10 mg per kilogram body weight of the recipient per day, preferably about 0.05–1 mg/kg/day. Thus, for administration to a 70 kg person, the dosage range would preferably be about 3.5 mg to 400 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from glycerol, propylene glycol, water, ethanol, and various oils, including those of petroleum, animal, vegetable or synthetic origin, e.g., peanut oil, soybean oil, mineral oil, sesame oil. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula I based on the total formulation, with the balance being one or more suitable pharmaceutical excipients. Preferably, the compound is present at a level of about 1–80 wt %. Representative pharmaceutical formulations containing a compound of Formula I are described in Example 3.

EXAMPLES

The following preparations and examples are given to enable those skilled in the art to more clearly understand and to practice the present invention. They should not be considered as limiting the scope of the invention, but merely as being illustrative and representative thereof.

Example 1

6-Methanesulfonyl-3-(4-methoxy-phenoxy)-benzo[b]thiophene-2-carbonitrile

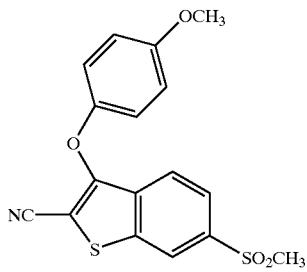

Steps 1–3

A solution of 4-methylsulfanylbenzaldehyde 1 (10 g, 66 mmol), (MeO)$_3$CH (8.6 mL, 79 mmol) and p-TsOH (0.25 g, 1.3 mmol) in MeOH (130 mL) was stirred for 18 h. The remaining pTsOH was decomposed by addition of NaOMe. After 5 min, the mixture was evaporated in vacuo, and passed through a pad of SiO$_2$ (95:5 hexane/Et$_2$O) to afford 1-(1,1-dimethoxy-methyl)-4-methylsulfanyl-benzene 2. The residue after evaporation was dissolved into CH$_2$Cl$_2$ (360 mL) and treated with MCPBA (41 g, 240 mmol). After 18 h, the mixture was filtered and the filtrate evaporated. The residue was partitioned between EtOAc and 1 M NaOH. The organic layer was washed with 1 M NaOH (2×), washed with brine, dried (MgSO$_4$), filtered and evaporated to afford 1-(1,1-dimethoxy-methyl)-4-methanesulfonylbenzene 3. The residue was dissolved into THF (130 mL) and treated with 2% H$_2$SO$_4$ (3.4 mL). After 2 h, the solvent was evaporated, and the residue was partitioned between EtOAc and NaHCO$_3$. The organic layer was dried (MgSO$_4$), filtered and evaporated to afford 12 g (98% for three steps) of 4-methylsulfonylbenzaldehyde 4 as a white solid; $^1$H NMR δ 3.11 (s, 3H), 8.09 (d, 2H, J=8.6), 8.14 (d, 2H, J=8.6), 10.15 (s, 1H).

Step 4

A solution of aldehyde 4-methylsulfonylbenzaldehyde 4 (1.0 g, 5.9 mmol) and malonic acid (0.63 g, 6.0 mmol) in 10:1 EtOH/pyridine (12.1 mL) was heated at a gentle reflux for 24 h. After cooling to 0° C., the resulting precipitate was collected and rinsed with cold Et$_2$O. The solid was resuspended in EtOH (13 mL) and heated at reflux for an additional 2 h. After cooling to 0° C., the resulting precipitate was collected and dried in vacuo to afford 0.63 g (51%) of 3-(4-methanesulfonyl-phenyl)-acrylic acid 5 as a white solid; $^1$H NMR (DMSO) δ 3.18 (s, 3H), 6.65 (d, 1H, J=16.1), 7.60 (d, 1H, J=16.1), 7.89 (m, 4H).

Steps 5–6

A stirring slurry of 3-(4-methanesulfonyl-phenyl)-acrylic acid 5 (3.7 g, 16 mmol), pyridine (0.13 mL, 0.13 g, 1.6 mmol), and DMF (1.2 mL, 1.1 g, 15 mmol) in phenylchloride (23 mL) was treated with SOCl$_2$ (6.1 mL, 9.9 g, 84 mmol). The resulting mixture was heated at reflux for 24 h. All volatile material was removed in vacuo to afford the intermediate acid chloride 6 as an orange solid; $^1$H NMR δ 3.15 (s, 3H), 8.06 (dd, 1H, J=1.5, 8.6), 8.23 (dd, 1H, J=0.6, 8.7), 8.53 (m, 1 H). The was dissolved into CH$_2$Cl$_2$ (50 mL), cooled to 0° C., and treated with 0.5 m solution of NH$_3$ in 1,4 dioxane(12 mL). After 30 min, the resulting solid was collected to afford 3.5 g (74%) of 3-chloro-6-methanesulfonyl-benzo[b]thiophene-2-carboxylic acid amide 7; $^1$H NMR (DMSO) δ 3.31 (s, 3H), 8.00 (brs, 1H), 8.06 (dd, 1H, J=1.6, 8.6), 8.13 (dd, 1H, J=0.7, 8.6), 8.24 (br s, 1H), 8.80 (dd, 1H, J=0.7, 1.6).

Step 7

A stirring 0° C. slurry of 3-chloro-6-methanesulfonyl-benzo[b]thiophene-2-carboxylic acid amide 7 (2.8 g, 9.7 mmol) in CH$_2$Cl$_2$ (50 mL) was treated by sequential addition of TFAA (4.0 mL, 5.9 g, 28 mmol) then pyridine (4.0 mL, 3.9 g, 49 mmol). After 2 h, the resulting solution was washed with 0.1 M HCl, dried (Na$_2$SO$_4$), filtered, and evaporated. Chromatography gave 2.1 g (81%) of 3-chloro-6-methanesulfonyl-benzo[b]thiophene-2-carbonitrile 8; $^1$H NMR δ 3.15 (s, 3H), 8.09 (dd, 1H, J=1.5, 8.6), 8.15 (dd, 1H, J=0.7, 8.6), 8.52 (dd, 1H, J=0.7, 1.5).

Step 8

A solution of KHMDS (0.18 g, 0.90 mmol) in DMF (7 mL) was treated by sequential addition of 4-methoxyphenol (0.12 g, 0.99 mmol) then 3-chloro-6-methanesulfonyl-benzo[b]thiophene-2-carbonitrile 8 (0.20 g, 0.75 mmol). After 2 h, the mixture was partitioned between EtOAc and brine. The organic layer was washed with brine (2×), dried (Na$_2$SO$_4$), filtered, and evaporated. Chromatography, followed by recrystallization (EtOAc/hexane) gave 0.20 g (74%) of 6-methanesulfonyl-3-(4-methoxy-phenoxy)-benzo[b]thiophene-2-carbonitrile 15 as white needles; (m+H)$^+$ 360.

Similarly, following the procedure described above, but replacing, in Step 8, 4-methoxyphenol with the appropriate substituted phenols or thiophenols the additional compounds of Formula I wherein Y is —S— and A is —O— or —S—, were prepared:

4-Methoxythiophenol gave 6-methanesulfonyl-3-(4-methoxy-phenylsulfanyl)benzo[b]thiophene-2-carbonitrile 16; (m+H)$^+$ 376;

2-Chlorothiophenol gave 3-(2-chloro-phenylsulfanyl)-6-methanesulfonyl-benzo[b]thiophene-2-carbonitrile 17; (m+H)$^+$ 380;

4-Methylthiophenol gave 6-Methanesulfonyl-3-p-tolylsulfanylbenzo[b]thiophene-2-carbonitrile 18; (m+H)$^+$ 360;

2,4-Dichlorothiophenol gave 3-(2,4-dichloro-phenylsulfanyl)-6-methanesulfonyl-benzo[b]thiophene-2-carbonitrile 19; (m+H)$^+$ 415;

4-Fluorophenol gave 3-(4-fluoro-phenoxy)-6-methanesulfonyl-benzo[b]thiophene-2-carbonitrile 20; (m+H)$^+$ 348;

Thiophenol gave 6-methanesulfonyl-3-phenylsulfanyl-benzo[b]thiophene-2-carbonitrile 21; (m+H)$^+$ 345;

4-Methylphenol gave 6-methanesulfonyl-3-p-tolyloxy-benzo[b]thiophene-2-carbonitrile 22; (m+H)$^+$ 344;

4-Chlorothiophenol gave 3-(4-chloro-phenylsulfanyl)-6-methanesulfonyl-benzo[b]thiophene-2-carbonitrile 23; (m+H)$^+$ 380;

Phenol gave 6-methanesulfonyl-3-phenoxy-benzo[b]thiophene-2-carbonitrile 24; (m+H)$^+$ 330;

2-Chloro-4-methoxyphenol gave 3-(2-chloro-4-methoxy-phenoxy)-6-methanesulfonyl-benzo[b]thiophene-2-carbonitrile 25; (m+H)$^+$ 394;

4-Fluorothiophenol gave 3-(4-fluoro-phenylsulfanyl)-6-methanesulfonyl-benzo[b]thiophene-2-carbonitrile 26; (m+H)$^+$ 364;

2-Fluorophenol gave 3-(2-fluoro-phenoxy)-6-methanesulfonyl-benzo[b]thiophene-2-carbonitrile 27; (m+H)$^+$ 348;

2,6-Dichlorothiophenol gave 3-(2,6-dichloro-phenylsulfanyl)-6-methanesulfonyl-benzo[b]thiophene-2-carbonitrile 28; (m+H)+ 415;

2-Methoxyphenol gave 6-methanesulfonyl-3-(2-methoxy-phenoxy)-benzo[b]thiophene-2-carbonitrile 29; (m+H)+ 360;

2-Fluorothiophenol gave 3-(2-fluoro-phenylsulfanyl)-6-methanesulfonyl-benzo[b]thiophene-2-carbonitrile 30; (m+H)+ 364;

4-Ethoxyphenol gave 3-(4-ethoxy-phenoxy)-6-methanesulfonyl-benzo[b]thiophene-2-carbonitrile 31; (m+H)+ 374;

2,4-Difluorothiophenol gave 3-(2,4-difluoro-phenylsulfanyl)-6-methanesulfonyl-benzo[b]thiophene-2-carbonitrile 32; (m+H)+ 382;

4-Chloro-2-fluorophenol gave 3-(4-chloro-2-fluoro-phenoxy)-6-methanesulfonyl-benzo[b]thiophene-2-carbonitrile 33; (m+H)+ 382;

2,4-Difluorophenol gave 3-(2,4-difluoro-phenoxy)-6-methanesulfonyl-benzo[b]thiophene-2-carbonitrile 34; (m+H)+ 366.

Example 2

6-Methanesulfonyl-3-(4-methoxy-phenyisulfanyl)-benzofuran-2-carbonitrile

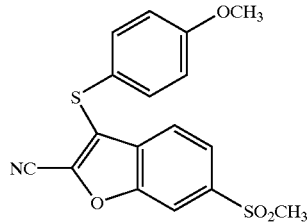

Step 1

A stirring solution of 2-methoxy-4-methylthiobenzoic acid 9 (50.0 g) in methanol (400 mL) was treated with concentrated $H_2SO_4$ (5 mL) under an inert atmosphere. After 1 day at 50° C., the mixture was cooled and the solvent was evaporated. The resulting oil was passed through a pad of silica gel (EtOAc) to afford, after concentration, 60 g of an oil. A portion of the oil (20 g) was dissolved into 10:1 MeOH/$H_2O$ (385 mL) and treated at 0° C. with Oxone™ (110 g, added in three portions) with vigorous stirring. After 2 h, the mixture was partitioned between EtOAc and $H_2O$. The organic layer was dried ($MgSO_4$) and passed through a pad of silica gel. The solvent was evaporated giving 21 g of 4-methanesulfonyl-2-methoxybenzoic acid methyl ester 10.

Step 2

A mixture of 10 (15 g) and pyridinium hydrochloride (45 g) was heated under an inert atmosphere at 180° C. for 1.5 h and cooled. The mixture was partitioned between EtOAc and aqueous HCl (5%). The organic layer was washed with aqueous HCl (5%), dried, filtered, and concentrated. A solution of the resulting residue in EtOH (400 mL) was treated with concentrated $H_2SO_4$ (10 mL) and heated overnight at 75° C. After cooling, the mixture was concentrated and partitioned between EtOAc and saturated aqueous $NaHCO_3$. The organic layer was extracted with 1 M NaOH (4 times). This combined aqueous layer was brought to acidic pH by addition of aqueous HCl (5%) and was extracted with EtOAc. This organic layer was dried ($MgSO_4$), filtered, and evaporated giving 8.5 g of 2-hydroxy-4-methanesulfonyl-benzoic acid ethyl ester 11 as a solid.

Step 3

A stirring solution of 11 (6.0 g) in DMF (200 mL) was treated with $K_2CO_3$ (6 g) and chloroacetonitrile (6 mL) and heated at 75° C. overnight. The mixture was cooled and partitioned between 1:1 EtOAc/hexanes and $H_2O$. The organic layer was washed with 1 M NaOH, washed with brine, dried ($MgSO_4$), filtered, and evaporated. The residue was triturated with $Et_2O$/hexanes. The resulting solid was collected by filtration giving 6.6 g of 2-cyanomethoxy-4-methanesulfonyl-benzoic acid ethyl ester 12.

Step 4

A suspension of 12 (4.0 g) in toluene was treated with potassium tert-butoxide (30 mL, 1 M in tert-butanol) under an inert atmosphere. After heating at 110° C. for 1 h, the mixture was cooled and the resulting precipitate was collected by filtration. The precipitate was washed with $Et_2O$ (3 times) giving 5 g of 3-hydroxy-6-methanesulfonyl-benzofuran-2-carbonitrile 13 as a yellow solid.

Step 5

A suspension of 13 (3.9 g) in $CH_2Cl_2$ (200 mL) was treated with pyridine (10 mL), methanesulfonyl chloride (4 mL), and a catalytic amount of dimethylaminopyridine at 0° C., under an $N_2$ atmosphere, for 2 h. The reaction was allowed to warm to ambient temperature overnight. The reaction was partitioned between 1:1 $Et_2O$/hexanes and brine. The organic layer was dried ($MgSO_4$), filtered, and evaporated. The residue was purified by chromatography (silica gel, 1:1 EtOAc/hexanes) giving 1.05 g of methanesulfonic acid 2-cyano-6-methanesulfonyl-benzofuran-3-yl ester 14.

Step 6

A stirring solution of 14 (0.25 g) and 4-methoxybenzenethiol (0.4 g) in THF (20 mL) and DMF (5 mL) was treated with NaH (0.080 g). After 3 h, the reaction was quenched by careful addition of $H_2O$, then diluted with 1:1 EtOAc/hexanes. The organic layer was washed with saturated aqueous $NaHCO_3$, washed with water, washed with brine, dried ($MgSO_4$), filtered, and evaporated. Chromatography (silica gel, 20:80 to 33:67 EtOAc/hexanes) gave 0.11 g of 6-methanesulfonyl-3-(4-methoxyphenylsulfanyl)-benzofuran-2-carbonitrile 35 as a solid; (m+H)+ 360.

Similarly, following the procedure described above, but replacing, in Step 6, 4-methoxybenzenethiol with 2,4-difluorobenzenethiol, the additional compound of Formula I wherein Y is —O— and A is —S— was prepared:

3-(2,4-Difluoro-phenylsulfanyl)-6-methanesulfonyl-benzofuran-2-carbonitrile 36; (M)+=366.

Example 3

The following are representative pharmaceutical formulations containing a compound of Formula I.

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Injectable Formulation

The following ingredients are mixed to form an injectable formulation.

| Ingredient | Amount |
| --- | --- |
| compound of this invention | 0.4 mg |
| sodium acetate buffer solution, 0.4 M | 2.0 mL |
| HCl (1N) or NaOH (1N) | q.s. to suitable pH |
| water (distilled, sterile) | q.s. to 20 mL |

Example 4

Inhibition of COX I and COX II in vitro

The COX I and COX II inhibitory activity of compounds of this invention in vitro was determined using partially purified COX I and COX II enzymes, prepared as described in J. Barnett et al., *Biochim. Biophys. Acta*, 1209,130–139 (1994).

COX I and COX II samples were diluted with Tris-HCl buffer (50 mM Tris-HCl, pH 7.9) containing 2 mM EDTA and 10% glycerol and reconstituted by incubating first with 2 mM phenol for 5 minutes and then with 1 micromolar hematin for an additional 5 minutes. 125 µL of the reconstituted COX I or COX II enzyme were preincubated for 10 minutes at room temperature in a shaking water bath with the compounds of the invention dissolved in 2–15 µL of DMSO or the carrier vehicles (control samples). The enzyme reaction was initiated by adding 25 µL of 1-[14 C] arachidonic acid (80,000–100,000 cpm/tube; 20 micromolar final concentration) and the reaction was allowed to continue for an additional 45 seconds. The reaction was terminated by adding 100 µL is of 2N HCl and 750 µL water. An aliquot (950 µL) of the reaction mixture was loaded onto a 1 mL $C_{18}$ Sep-Pak column (J. T. Baker, Phillipsburg, N.J.) which had been previously washed with 2–3 mL methanol and equilibrated with 5–6 mL distilled water. Oxygenated products were quantitatively eluted with 3 mL of acetonitrile/water/acetic acid (50:50:0.1, v/v) and the radioactivity in the eluate determined in a scintillation counter. Compounds of this invention were active in this assay for COX II.

The COX inhibitory activities (expressed as $IC_{50}$, the concentration causing 50% inhibition of the COX enzyme being assayed) of some exemplary compounds of the invention were:

| CPD # | COX I $IC_{50}$, µM | COX II $IC_{50}$, µM |
| --- | --- | --- |
| 17 | >120 | <1.0 |
| 19 | >120 | <1.5 |
| 26 | >120 | <1.5 |
| 30 | >120 | <1.2 |
| 31 | >120 | <1.5 |

Example 5

Anti-inflammatory Activity

The anti-inflammatory activity of compounds of this invention was determined by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" *Proc. Soc. Exp. Biol. Med.* 111, 544–1962). This assay has been used as a primary in vivo screen for anti-inflammatory activity of most NSAIDs, and is considered predictive of human efficacy. Briefly, test materials were administered orally to female rats in a volume of 1 mL prepared as solutions or suspensions in an aqueous vehicle containing 0.9% sodium chloride, 0.5% sodium carboxymethyl-cellulose, 0.4% polysorbate 80, 0.9% benyl alchol and 97.3 distilled water. Control rats received vehicle alone. After 1 h 0.05 mL of a 0.5% solution of Carrageenan (Type IV Lambda, Sigma Chemical Co.) in 0.9% saline was injected into the subplantar region of the right hind paw. Three hours later the rats were euthanized in a carbon dioxide atmosphere; hind paws were removed by severing at the tatso-crural joint; and the left and right paws were weighted. The increase in weight of the right paw over the left paw was obtained for each animal and the mean increases were calculated for each group. The anti-inflammatory activity of the test materials is expressed as the percent inhibition of the increase in hind paw weight of the test group relative to the vehicle dosed control group.

Compounds of this invention were active in this assay.

Example 6

Inhibition of Eicosanoid Synthesis in Vivo

The activity of compounds of this invention in inhibiting in vivo eicosanoid (prostaglandin $E_2$) synthesis in inflamed tissues was determined by the carrageenan-induced inflammation (air-pouch model) in rats, using a modification of the method described in Futaki, M., et al., "Selective Inhibition of NS-398 on prostanoid production in inflamed tissue in rat Carrageenan Air-pouch Inflammation" *J. Pharm. Pharmacol.* 45, 753–755, (1993) and Masferrer, J. L., et al.; "Selective Inhibition of inducible cyclooxygenase 2 in vivo is Antiflammatory and Nonulcerogenic" *Proc. Natl. Acad. Sci. U.S.A.* 91, 3228–3232, (1994). In this assay, an air-pouch is created in the rat and the $PGE_2$ levels in the air-pouch exudate are measured by enzyme immunoassay. Briefly, male rats were anesthetized using a 60:40 $CO_2:O_2$ mixture and subsequently injected subcutaneously with 20 mL of sterilized air, under aseptic conditions, in the proximal area of the dorsum. This injection of sterile air causes the creation of a subcutaneous "air pouch". The next day, a further 10 mL of sterile air was injected into the previously formed pouch using the same technique. The test materials were administered orally in a volume of 1 mL/100 g body weight as solutions or suspensions in an aqueous vehicle containing 0.9% sodium chloride, 0.5% sodium carboxymethyl-cellulose, 0.4% polysorbate 80, 0.9% benzyl alcohol and 97.3% water. Control rats received vehicle alone. After 30 minutes, 5 mL of a 0.5% solution of carrageenan (Sigma, Lambda Type IV) was injected into the air pouch. The rats were euthanized 3 or 6 h after the compound administration. 10 mL of a solution containing 10 µg/l of indomethacin and 5.4 mM EDTA in 0.9% sterile saline was injected into the air pouch; the air pouch was cut open; and the exudate was harvested. The total exudate volume was recorded, and the samples were analyzed for $PGE_2$ and 6-keto $PGF_1$ by ELISA (Titerzyme®, PerSeptive Diagnostics, Boston, Mass.) and $TxB_2$ by radioimmuno assay (New England Nuclear Research, Boston Mass., Catalog No. NEK-037), according to the manufacturer's directions.

The mean concentrations of $PGE_2$ were calculated for each group. The anti-inflammatory activity of test materials is expressed as the percent inhibition of $PGE_2$ formation in the test group relative to the control group.

Compounds of this invention were active in this assay.

Example 7

Analgesic Activity

The analgesic activity of the compounds of this invention may be determined by using a modification of the method described in Randall, L. O., and Selitto, J. J., "A Method for Measurement of Analgesic Activity on Inflamed Tissue", *Arch. Int. Pharmacodyn.*, CXI, 4, 409, (1957) and Gans, et. al., "Anti-inflammatory and Safety Profile of DuP 697, a Novel Orally Effective Prostaglandin Synthesis Inhibitor", *J. Pharmcol. Exp. Ther.*, 254, No. 1, 180, (1990). In this assay, the male Sprague Dawley rats were injected with 0.1 mL of 20% brewer's yeast in deionized water (Sigma, St. Louis) in the subplantar region of the left hind foot. After 2 h, the test materials were administered orally in a volume of 1 mL/100 g body weight as solutions or suspensions in an aqueous vehicle containing 0.9% sodium chloride, 0.5% sodium carboxymethyl-cellulose, 0.4% polysorbate 80, 0.9% benzyl alcohol and 97.3% water. Control rats received vehicle alone. After 1 h, the hindpaw was placed on the platform of a Basile Analgesy-Meter (Ugo Biological Research Apparatus, Italy, Model #7200) and mechanical force was applied to the dorsum of the rat's hindpaw. Compounds of the invention were active in this assay.

The analgesic activity of compounds of this invention may also be determined by using an adjuvant-induced arthritis pain model in the rat, where pain is assessed by the animal's vocal response to the squeezing or flexing of an inflamed ankle joint, as described in Winter C. A. and Nuss, G. W., "Treatment of Adjuvant Arthritis in rats with Anti-inflammatory Drugs", *Arthritis Rheum.*, 9, 394–403, (1966) and Winter, C. A., Kling P. J., Tocco, D. J., and Tanabe, K., "Analgesic activity of Diflunisal [MK-647; 5-(2,4-Difluorophenyl)salicylic acid] in Rats with Hyperalgesia Induced by Freund's Adjuvant", *J. Pharmacol. Exp. Ther.*, 211, 678–685, (1979).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications, and publications cited in this application are hereby incorporated by reference in their entirety for all purposes to the same extent as if each individual patent, patent application, or publication were so individually denoted.

What is claimed is:

1. A compound selected from the group of compounds represented by Formula I

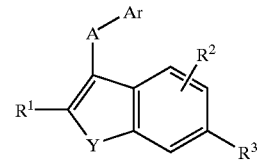

wherein

Y is O or S;

A is a —$CH_2$—, —C(O)—, —O—, —S—, —S(O)—, or —$S(O)_2$—;

Ar is an optionally substituted phenyl;

$R^1$ is hydrogen, alkyl, alkoxy, hydroxy, halo, cyano, —C(O)$NR^4R^5$, —$COOR^4$, —$NR^4R^5$, wherein $R^4$ and $R^5$ are each independently in each occurrence hydrogen or alkyl;

$R^2$ is hydrogen, alkyl, alkoxy, hydroxy, halo, haloalkyl, nitro, cyano, or —$NR^4R^5$, wherein $R^4$ and $R^5$ are as defined previously;

$R^3$ is —$SR^6$, —$SOR^6$, —$SO_2R^6$, or —$SO_2NR^4R^5$ wherein $R^6$ is alkyl, hydroxyalkyl, alkoxyalkyl, carboxyalkyl, or alkoxycarbonylalkyl; and $R^4$ and $R^5$ are as defined previously; or prodrugs, individual isomers, mixtures of isomers, and pharmaceutically acceptable salts thereof.

2. The compound of claim 1 wherein Ar is phenyl optionally substituted at one or two substitutents independently selected from the group consisting of halo and alkoxy, and $R^3$ is —$SO_2R^6$, wherein $R^6$ is alkyl.

3. The compound of claim 2 wherein Y is —O— and A is —S—.

4. The compound of claim 3 wherein $R^1$ is alkyl or cyano.

5. The compound of claim 2 wherein Y is —S— and A is —S—.

6. The compound of claim 5 wherein $R^1$ is alkyl or cyano.

7. The compound of claim 2 wherein Y is —S— and A is —O—.

8. The compound of claim 7 wherein $R^1$ is alkyl or cyano.

9. The compound of claim 1 selected from the group consisting of:

3-(2-Chloro-phenylsulfanyl)-6-methanesulfonyl-benzo[b]thiophene-2-carbonitrile;

3-(2,4-Dichloro-phenylsulfanyl)-6-methanesulfonyl-benzo[b]thiophene-2-carbonitrile;

3-(4-Ethoxy-phenoxy)-6-methanesulfonyl-benzo[b]thiophene-2-carbonitrile;

3-(2-Fluoro-phenylsulfanyl)-6-methanesulfonyl-benzo[b]thiophene-2-carbonitrile;

3-(4-Fluoro-phenylsulfanyl)-6-methanesulfonyl-benzo[b]thiophene-2-carbonitrile; and 3-(4-Chloro-2-fluoro-phenoxy)-6-methanesulfonyl-benzo[b]thiophene-2-carbonitrile.

10. A pharmaceutical composition comprising a therapeutically effective amount of a compound of claim 1 and a pharmaceutically acceptable excipient.

11. A method of treatment of a disease in a mammal treatable by administration of a selective COX II inhibitor comprising administration to the mammal a therapeutically effective amount of a compound of claim 1.

12. The method of claim 11 wherein the disease is an inflammatory disease selected from myositis, synovitis, arthritis, gout, back pain, dental pain, sports injuries, sprains, strains, headache, tendonitis, ankylosing, sponylitis, and bursitis.

13. The method of claim 11 wherein the disease is dysmenorrhoea or premature labor.

14. The method of claim 11 wherein the disease is Alzheimer's.

15. A process for preparing a compound selected from the group of compounds of claim 1, which comprises reacting a compound of general Formula:

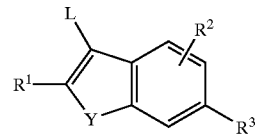

wherein L is a leaving group, and $R^1$, $R^2$, $R^3$, and Y are as defined in claim 1 with a compound of general formula ArAH, wherein Ar and A are as defined in claim 1, to provide a compound of Formula I:

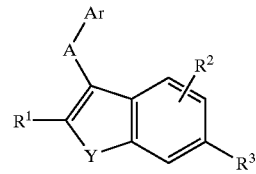

wherein $R^1$, $R^2$, $R^3$, Y, A and Ar are as defined in claim 1.

16. The method of claim 12 wherein the disease is rheumatoid arthritis or osteoarthritis.

* * * * *